United States Patent
Sato (10) Patent No.: US 8,317,680 B2
(45) Date of Patent: Nov. 27, 2012

(54) ENDOSCOPE APPARATUS AND CONNECTION UNIT THEREFOR

(75) Inventor: Saichi Sato, Sagamihara (JP)

(73) Assignee: Olympus Corporation, Tokyo (JP)

( * ) Notice: Subject to any disclaimer, the term of this patent is extended or adjusted under 35 U.S.C. 154(b) by 27 days.

(21) Appl. No.: 12/902,289

(22) Filed: Oct. 12, 2010

(65) Prior Publication Data

US 2011/0243323 A1   Oct. 6, 2011

Related U.S. Application Data (63) Continuation of application No. PCT/JP2010/056027, filed on Apr. 1, 2010.

(51) Int. Cl.
*A61B 1/00* (2006.01)

(52) U.S. Cl. .......... 600/109; 600/118; 600/132

(58) Field of Classification Search .......... 600/101, 600/109, 118, 132; 348/65, 74–76
See application file for complete search history.

(56) References Cited

U.S. PATENT DOCUMENTS

| | | | |
|---|---|---|---|
| 6,538,687 B1* | 3/2003 | Saito et al. | 348/65 |
| 6,993,167 B1* | 1/2006 | Skladnev et al. | 382/128 |
| 7,128,709 B2 | 10/2006 | Saruya | |
| 7,855,727 B2* | 12/2010 | Adler et al. | 348/65 |
| 7,956,888 B2* | 6/2011 | Karpen | 348/85 |
| 2001/0051766 A1* | 12/2001 | Gazdzinski | 600/309 |
| 2003/0236446 A1* | 12/2003 | Eino | 600/160 |
| 2004/0171913 A1* | 9/2004 | Saruya | 600/132 |
| 2005/0166044 A1* | 7/2005 | Kanai et al. | 713/157 |
| 2008/0064925 A1* | 3/2008 | Gill et al. | 600/109 |
| 2008/0187133 A1* | 8/2008 | Akima | 380/28 |
| 2009/0030315 A1* | 1/2009 | Hibi | 600/443 |
| 2009/0036742 A1* | 2/2009 | Watanabe | 600/178 |

FOREIGN PATENT DOCUMENTS

| | | |
|---|---|---|
| JP | 04-081188 A | 3/1992 |
| JP | 04-158828 A | 6/1992 |
| JP | 11-089791 A | 4/1999 |
| JP | 2000-267018 A | 9/2000 |
| JP | 2004-126570 A | 4/2004 |
| JP | 2005-131320 A | 5/2005 |
| JP | 2007-111358 A | 5/2007 |
| JP | 2009-006118 A | 1/2009 |

OTHER PUBLICATIONS

International Search Report dated Jun. 15, 2010 in counterpart International Application No. PCT/JP2010/056027.

* cited by examiner

*Primary Examiner* — John P Leubecker
*Assistant Examiner* — Arnaldo Torres Diaz
(74) *Attorney, Agent, or Firm* — Holtz, Holtz, Goodman & Chick, PC (57) ABSTRACT

An endoscope apparatus includes an endoscope apparatus body portion which includes a first connector, and which is connectable to an insertion portion having an image pickup device disposed at a distal end portion. The endoscope apparatus further includes a connection unit which includes a second connector which is removably connectable to the endoscope apparatus body portion by communicating the second connector with the first connector, a non-volatile memory which stores a program for processing image data inputted from the image pickup device via the second connector, a CPU which controls the processing of the image data in accordance with the stored program to produce processed data, and a display data output section configured to output the processed data.

20 Claims, 9 Drawing Sheets

ENDOSCOPE APPARATUS AND CONNECTION UNIT THEREFOR

CROSS REFERENCE TO RELATED APPLICATION

This application is a continuation application of PCT/JP2010/056027 filed on Apr. 1, 2010, the entire contents of which are incorporated herein by this reference.

BACKGROUND OF THE INVENTION

1. Field of the Invention

The present invention relates to an endoscope apparatus and connection unit therefor.

2. Description of the Related Art

Conventionally, endoscope apparatuses have been used widely not only in the medical field, but also in the industrial field. For example, in the industrial field, endoscope apparatuses are used to inspect blades in engines of aircraft. The endoscope apparatus includes an insertion portion whose distal end portion is provided with an image pickup device. A user can bring the image pickup device provided in the distal end portion of the insertion portion close to a subject and display an image picked up by the image pickup device on a monitor. Also, the endoscope apparatus can not only display the image of the subject on a monitor when the image is picked up by the image pickup device provided in the distal end portion of the insertion portion, but can also store image data of the image in a storage device.

For example, as disclosed in Japanese Patent Application Laid-Open Publication No. 2009-6118, some endoscope apparatuses allow a storage medium such as a memory card to be loaded into an apparatus body, and consequently the user can record picked up image data, on a storage medium serving as an external memory.

SUMMARY OF THE INVENTION

The present embodiment provides an endoscope apparatus including an endoscope apparatus body portion which includes a first connector, and which is connectable to an insertion portion having an image pickup device disposed at a distal end portion thereof; and a connection unit. The connection unit includes: a second connector which is removably connectable to the endoscope apparatus body portion by communicating the second connector with the first connector; a non-volatile memory which stores a program for processing image data inputted from the image pickup device via the second connector; a CPU which controls the processing of the image data in accordance with the stored program to produce processed data; and a display data output section configured to output the processed data.

DETAILED DESCRIPTION OF THE PREFERRED EMBODIMENT

An embodiment of the present invention will be described below with reference to the drawings.

(Configuration)

Figure 1:
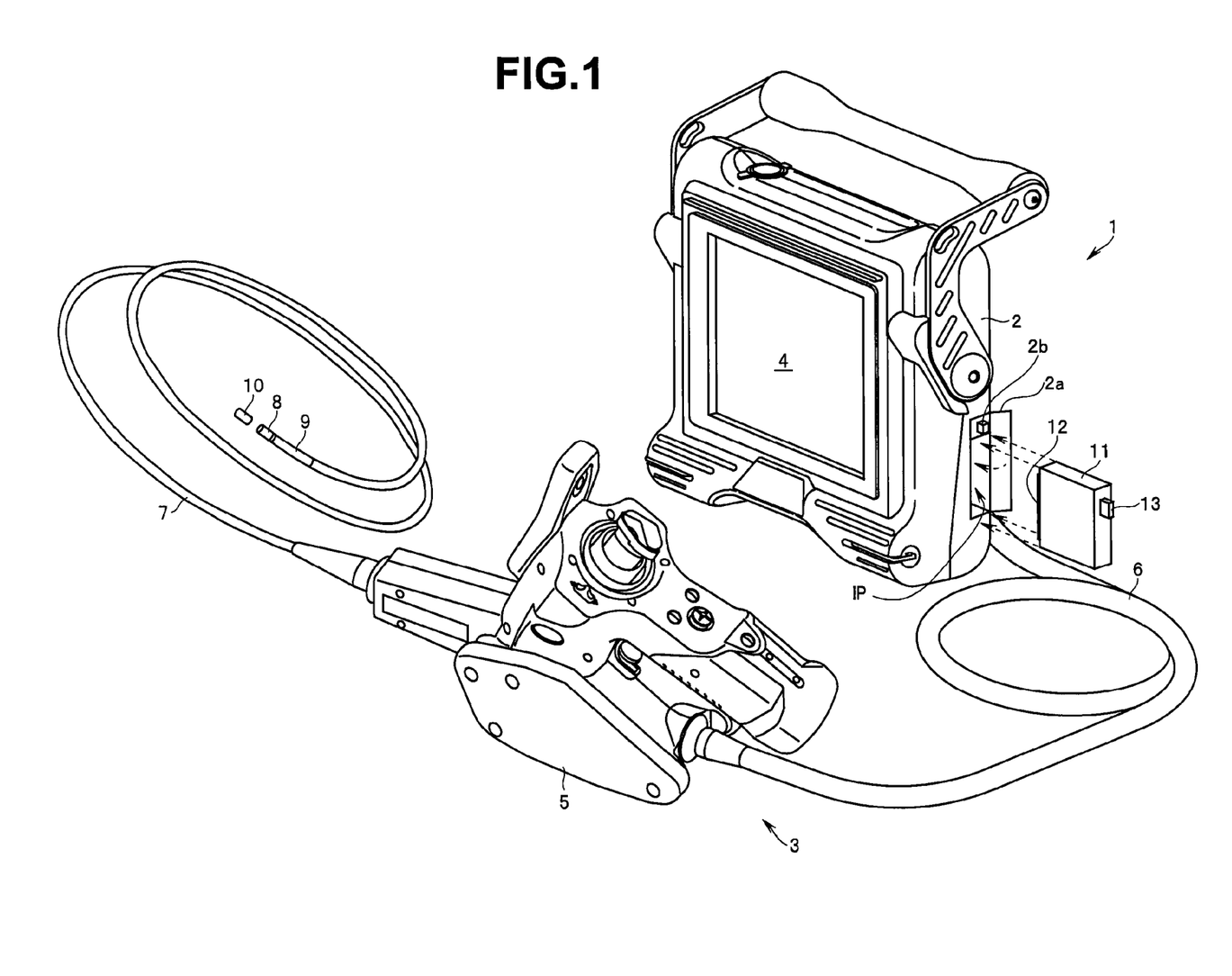
FIG. 1 is an external view of an endoscope apparatus according to an embodiment of the present invention.

First, a configuration of an endoscope apparatus according to the present embodiment will be described below with reference to FIG. 1. FIG. 1 is an external view of the endoscope apparatus according to the present embodiment.

As shown in FIG. 1, the endoscope apparatus 1 includes a body portion 2 which is a main unit and a scope unit 3 which is connected to the body portion 2. The body portion 2 includes a liquid crystal panel (hereinafter abbreviated to LCD) 4 serving as a display device which displays endoscopic images, an operation menu, and the like. The LCD 4 is equipped with a touch panel (FIG. 3) as described later. The scope unit 3 includes an operation section 5 and a body portion 2 interconnected by a universal cable 6 which is a connection cable and further includes an insertion portion 7 made of a flexible insertion tube. Thus, the insertion portion 7 can be connected to the body portion 2 via the operation section 5 of the scope unit 3 and the universal cable 6.

Incidentally, although the LCD 4 is provided on the body portion 2 in FIG. 1, the LCD 4 may be provided separately from the body portion 2 and connected via a connection cable or the like.

A camera is provided in a distal end portion 8 of an insertion portion 7. Specifically, the distal end portion 8 incorporates an image pickup device (not shown) such as a CCD or CMOS. Also, an image pickup optical system including lenses is placed on the side of an image pickup surface of the image pickup device. A bending portion 9 is provided on a proximal side of the distal end portion 8. An optical adaptor 10 can be installed in the distal end portion 8. The operation section 5 is provided with various operation buttons including a release button and an up, down, left, and right (U/D/L/R) directional bending button.

The endoscope apparatus 1 may be used to inspect the insides of engines at automobile manufacturing plants, to inspect turbine blades in jet engines at airports, and the like. The user can capture live images of a subject or record still images by operating various operation buttons of the operation section 5. Also, the user can specify various operations of the endoscope apparatus 1 by operating the touch panel. That is, the touch panel comprises a command input section used to specify concrete operations of the endoscope apparatus 1.

Using the touch panel for the operation section 5 allows a novice at endoscopy to operate the endoscope apparatus 1 more easily than when a joystick is used for the operation section 5.

The core unit 11 serving as a connection unit can be detachably attached to the body portion 2. That is, the core unit 11 can be connected to the body portion 2. The user can attach and remove the core unit 11 to/from the body portion 2.

The core unit 11 as a connection unit is equipped with a single-chip semiconductor device containing a central processing unit (hereinafter referred to as a CPU) as described later. The single-chip semiconductor device contains a nonvolatile memory such as a flash memory as a built-in memory. Incidentally, the built-in memory does not necessarily have to be incorporated in the single-chip semiconductor device itself as long as the built-in memory is provided in the core unit 11. For example, the built-in memory may be mounted as a semiconductor device on a board on which another semiconductor device incorporating a CPU has been mounted. Also, a memory card 14 (FIG. 2) serving as an external memory can be loaded into the core unit 11 as described later.

In a lateral portion, the body portion 2 is provided with a lid portion 2a which can be opened and closed on a hinge mechanism. By opening the lid portion 2a of the body portion 2, the user can install and remove the core unit 11 in/from the body portion 2 through an insertion port IP. It is noted that the insertion port IP may alternately be provided elsewhere on the body portion 2. The core unit 11 has a connector 12 for connecting to and communicating with a connector 2d (FIG. 3) provided inside the body portion 2. As the connector 12 and the connector 2d are connected with each other, the core unit 11 is electrically connected to a camera, the LCD 4, the operation section 5, and the like of the endoscope apparatus 1. To remove the core unit 11 from the body portion 2, the user can press a eject button 2b on the body portion 2, bringing an eject mechanism into operation. Consequently, the connector 12 of the core unit 11 is removed from the connector 2d in the body portion 2, removing the core unit 11 from the body portion 2. Incidentally, although the body portion 2 and the core unit 11 are connected directly by means of connector connection between the connectors 12 and 2d, the connectors 12 and 2d may be connected with each other via a connection cable or the like.

The user can bring the distal end portion 8 of the insertion portion 7 of the endoscope apparatus 1 close to a target area for observation in an apparatus targeted for inspection, display endoscopic images on the LCD 4 and thereby inspect the target area.

Figure 2:
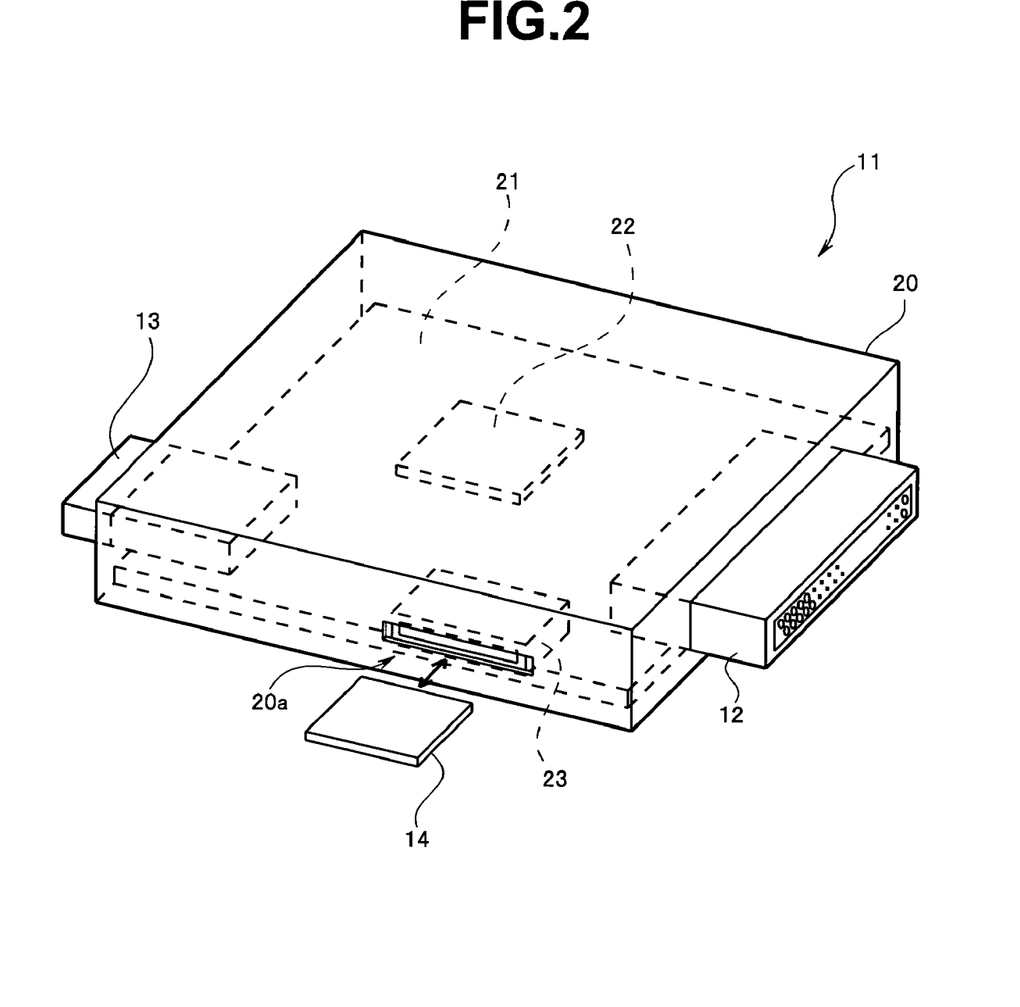
FIG. 2 is an external view of a core unit 11 according to the embodiment of the present invention.

FIG. 2 is an external view of the core unit 11. In this case, an enclosure 20 of the core unit 11 is made of resin and shaped approximately as a rectangular solid. The connector 12 is provided in protrusion on a lateral face of the enclosure 20. Furthermore, a USB connector 13 is provided in protrusion on a lateral face opposite the lateral face on which the connector 12 is provided.

A loading slot 20a for the memory card 14 is provided in another lateral face of the enclosure 20, and thus the memory card 14 can be loaded into the core unit 11 through the loading slot 20a. The USB connector 13 is a USB male connector which can be connected to a USB connector port of a computer (hereinafter referred to as a PC) such as an image data management computer or an image data saving computer. The USB connector 13 may be fixedly or retractably provided on the core unit 11.

The core unit 11 includes a board 21 which is fixed in the enclosure 20 and on which a single-chip semiconductor device 22 is mounted. The connector 12, the USB connector 13, and a memory card connector 23 are fixedly mounted on the board 21. The memory card 14 loaded through the loading slot 20a of the enclosure 20 is connected to the memory card connector 23. As the core unit 11 is attached to the body portion 2, the connector 12 is connected to the connector 2d in the body portion 2. That is, the connector 12 is intended to connect the core unit 11 to the body portion 2. The USB connector 13 is intended to connect the core unit 11 to the PC. The memory card connector 23 is intended to connect the memory card 14 to the core unit 11.

The core unit 11 is, for example, box-shaped, preferably measuring approximately 5 cm in width and depth, and approximately 1 cm in height, but may be formed in any size appropriate for communicating with the endoscope apparatus 1.

As described later, image data obtained using the endoscope apparatus 1 is inspection data on an inspection target and can be recorded by the endoscope apparatus 1 in the built-in memory and/or the memory card 14.

Figure 3:
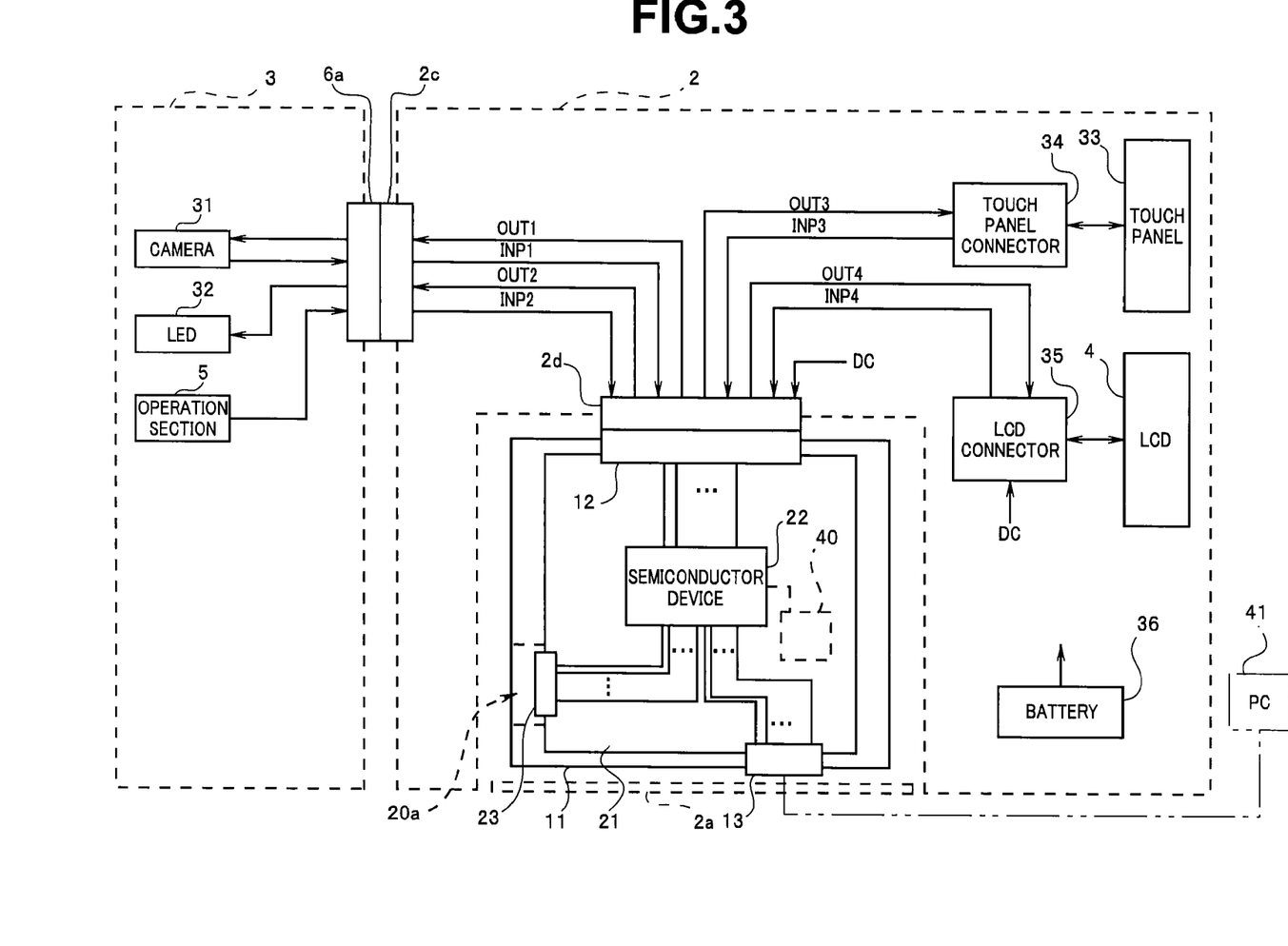
FIG. 3 is a block diagram illustrating a circuit configuration of the endoscope apparatus 1 according to the embodiment of the present invention.

FIG. 3 is a block diagram for illustrating a circuit configuration of the endoscope apparatus 1. The body portion 2 and the scope unit 3 are electrically connected when a connector 2c on the side of the body portion 2 is connected with a connector 6a on a proximal side of the universal cable 6 of the scope unit 3. On the other hand, the body portion 2 and the core unit 11 are electrically connected when the connector 2d provided in the body portion 2 is connected with the connector 12 of the core unit 11.

Also, a touch panel 33 and a touch panel connector 34 are provided in the body portion 2, where the touch panel connector 34 is used to connect the touch panel 33. The touch panel connector 34 is connected to the connector 2d. Furthermore, the LCD 4 and an LCD connector 35 are provided in the body portion 2, where the LCD connector 35 is used to connect the LCD 4. The LCD connector 35 is connected to the connector 2d.

As described later, the semiconductor device 22 mounted on the board 21 of the core unit 11 is a single-chip IC, i.e., a single-chip semiconductor device, which has functions of a camera control unit and a control section as well as control functions for the touch panel 33 and the LCD 4.

A camera 31 provided in the distal end portion 8 of the insertion portion 7 and an LED 32 which is an illuminating device are connected to the semiconductor device 22 via the connectors 12, 2d, 2c, and 6a. The operation section 5 is also connected to the semiconductor device 22 via the connectors 12, 2d, 2c, and 6a. The LCD 4 is connected to the semiconductor device 22 via the connectors 12, 2d, and 35. The touch panel 33 is connected to the semiconductor device 22 via the connectors 12, 2d, and 34.

A battery 36 is provided in the body portion 2. The battery 36 supplies power to the LCD connector 35 and various other circuits in the body portion 2 via a DC-DC converter (not shown). At the same time, the battery 36 similarly supplies power to the semiconductor device 22 and various other circuits in the core unit 11 via the connectors 2d and 12.

The single-chip semiconductor device 22 is mounted on the single board 21 and is connected with the camera 31, the LCD 4, and other devices via the connectors 12, 2d, 2c, and 6a. That is, the semiconductor device 22 is electrically connected with the camera 31 and other devices via wiring on the single board 21 as well as via signal cables connected to the wiring.

The semiconductor device 22 outputs various drive signals OUT1 to the camera 31, which in turn outputs various input signals INP1 including a video signal to the semiconductor device 22. In this case, the camera 31 is a CMOS sensor. As described later, the semiconductor device 22 contains a drive circuit to directly supply a drive signal to the camera 31 and directly receives an image pickup signal from the camera 31 including an image pickup device such as a CMOS sensor.

The LED 32 is provided in the distal end portion 8 of the insertion portion 7 as an illumination section which illuminates the subject to be observed and is connected via a DC drive circuit (not shown). The semiconductor device 22 outputs a drive signal OUT2 for the LED 32 to the DC drive circuit. The LED 32 is driven by an output from the DC drive circuit. The DC drive circuit (not shown) is mounted on a circuit board 21.

The operation section 5 is connected to the semiconductor device 22. The operation section 5 outputs an input signal INP2 to the semiconductor device 22, where the input signal INP2 includes various operation signals which represent concrete operations of the operation section 5.

The touch panel 33 is installed by being placed on a surface of the LCD 4 and is connected to the semiconductor device 22 via the touch panel connector 34 and a DC electrode drive circuit (not shown). The semiconductor device 22 outputs a drive signal OUT3 to the DC electrode drive circuit to drive each electrodes of the touch panel 33. Then, the touch panel 33 is driven by output from the DC electrode drive circuit via the touch panel connector 34. The DC electrode drive circuit (not shown) is mounted on the circuit board 21. The DC electrode drive circuit converts the drive signal OUT3 outputted from the semiconductor device 22 into a voltage signal suitable for driving each electrode of the touch panel 33.

An input signal INP3 which is a touch position detection signal from the touch panel 33 is inputted to the semiconductor device 22 via the touch panel connector 34. Thus, the semiconductor device 22 is electrically connected with the touch panel 33 via signal lines, includes a drive circuit to supply the drive signal OUT3 to the touch panel 33, and directly receives the input signal INP3 from the touch panel 33.

The LCD 4 is connected to the semiconductor device 22 via the LCD connector 35. DC power for backlight is supplied through the LCD connector 35. The semiconductor device 22 exchanges various command signals with the LCD 4, receives an input signal INP4 from the LCD 4, and outputs various drive signals OUT4 to the LCD 4. Thus, the semiconductor device 22 is electrically connected with the LCD 4 via signal lines and includes a drive circuit to supply the drive signals OUT4 directly to the LCD 4.

The touch panel connector 34 and the LCD connector 35 are fixed to a board or frame in the body portion 2.

The memory card 14 is a storage medium used to record endoscopic images and is connected to the semiconductor device 22 via the memory card connector 23. Thus, the memory card connector 23 allows an external memory to be attached.

As described above, to provide a semiconductor device of a non-volatile memory chip on the board 21 separately from the semiconductor device 22 which does not incorporate a non-volatile memory or to provide a non-volatile memory chip on the board 21 in addition to the semiconductor device 22 which incorporates another non-volatile memory, a non-volatile memory 40 such as a flash memory may be mounted on the board 21 as indicated by a dotted line in FIG. 3.

The battery 36 supplies power to one or more DC/DC circuits (not shown) in the body portion 2, and the DC/DC circuits supply necessary power to various circuits in the body portion 2 as well as to various circuits on the board 21 in the core unit 11.

Figure 4:
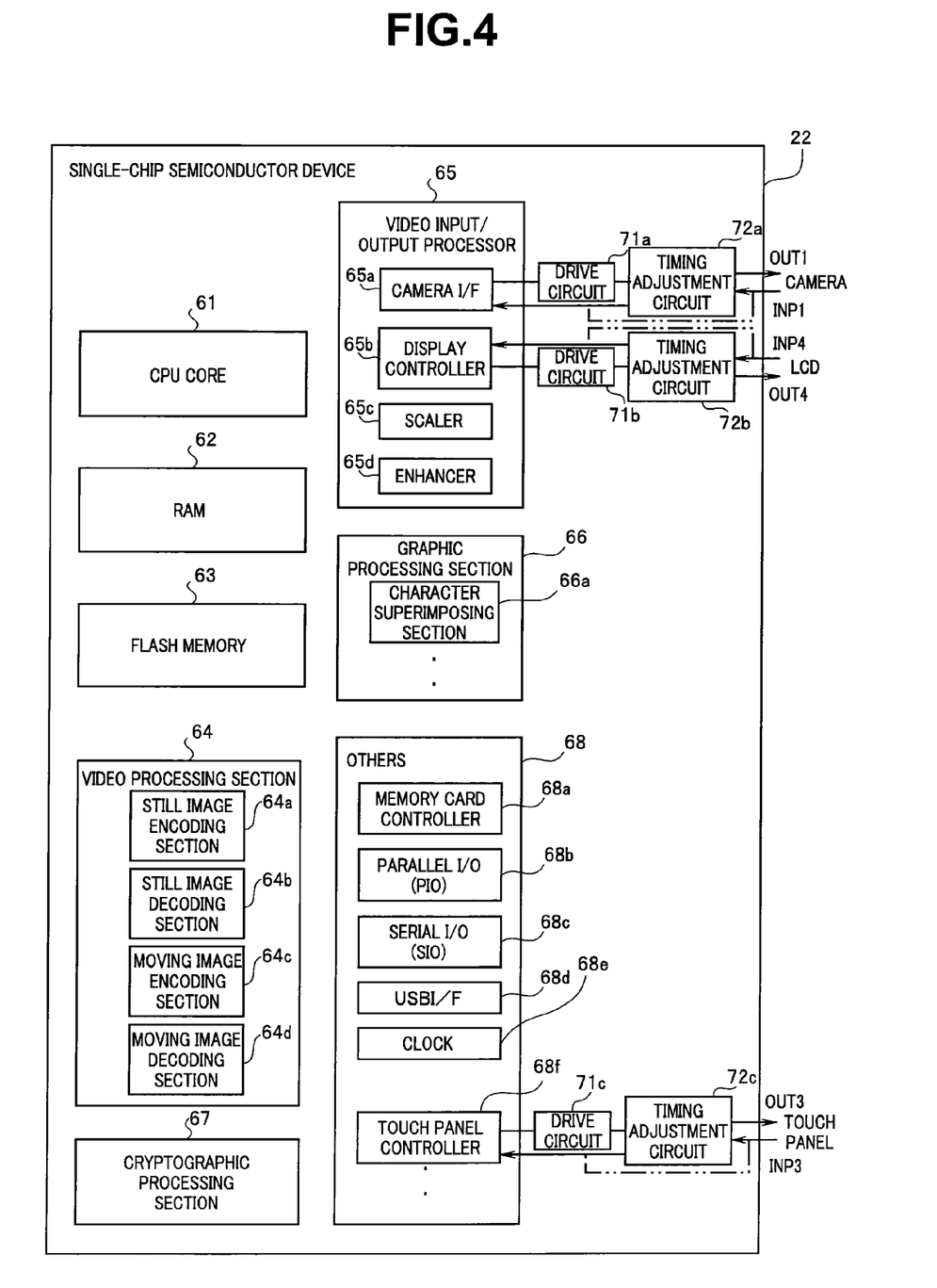
FIG. 4 is a block diagram showing an internal configuration of a semiconductor device 22 according to the embodiment of the present invention.

Next, contents of the semiconductor device 22 will be described with reference to FIG. 4. FIG. 4 is a block diagram showing an internal configuration of the semiconductor device 22.

The semiconductor device 22 is a single-chip IC as described above. The semiconductor device 22 contains a CPU core 61 serving as a CPU, a RAM 62, a flash memory 63 which is a non-volatile rewritable memory, a video processing section 64, a video input/output processor 65, a graphic processing section 66, a cryptographic processing section 67, and other circuits 68. The CPU core 61 and circuit sections are interconnected via an internal bus or a signal line group, and so are the circuit sections. As described above, the semiconductor device 22 controls the entire endoscope apparatus 1 and has functions of a conventional camera control unit. As described later, the semiconductor device 22 incorporates drive circuits and timing adjustment circuits for various devices. The incorporation of drive circuits and timing adjustment circuits for various devices in the semiconductor device 22 is preferable in terms of measures against EMC.

The CPU core 61 is a control section configured to perform various computations and other processes and performs operations of functions of the endoscope apparatus 1. The RAM 62 is a memory used as a working storage area for the CPU core 61. The flash memory 63 prestores various programs and various parameter data, including a program for controlling operation of the entire endoscope apparatus 1, a program for processing image pickup data of the image pickup device, and a program for setting adjustment parameters for the drive circuits and the timing adjustment circuits. Furthermore, the flash memory 63 records or temporarily saves image data processed by the program which processes the image pickup data. The program which sets adjustment parameters functions as a parameter setting section which sets various adjustment parameters. The CPU core 61 executes the processing programs and the like by loading the processing programs and the like into the RAM 62 from the flash memory 63.

Incidentally, the RAM 62 may be installed outside the semiconductor device 22.

The video processing section 64 is a circuit which processes moving images and still images picked up by the camera 31. The video processing section 64 includes a still image encoding section 64a, a still image decoding section 64b, a moving image encoding section 64c, and a moving image decoding section 64d. The video processing section 64 encodes inputted image data of still images in JPEG format or the like and moving images in MPEG4 format or the like, and decodes image data stored in the flash memory 63 which is a built-in memory or the memory card 14 which is an external memory. The encoded image data is stored in the flash memory 63 or a memory card 38 while the decoded image data is outputted to the LCD 4 to display images on a screen.

The video input/output processor 65 controls input and output of video data to/from the camera 31 and the LCD 4. The video input/output processor 65 includes a camera I/F 65a, a display controller 65b, a scaler 65c, an enhancer 65d, and the like.

The camera I/F 65a drives the camera 31 via a drive circuit 71a and timing adjustment circuit 72a for the camera 31 and receives an image pickup signal via the timing adjustment circuit 72a.

If the image pickup signal from the camera 31 is an analog signal, the timing adjustment circuit 72a includes an A/D converter which receives the image pickup signal.

The drive circuit 71a outputs the drive signal OUT1 at a voltage corresponding to set adjustment parameter data to drive the camera 31.

The timing adjustment circuit 72a is provided in the semiconductor device 22 and intended to adjust drive signal output timing of the drive circuit 71a. Also, the timing adjustment circuit 72a adjusts input timing of an input signal from the camera 31. The timing adjustment circuit 72a adjusts the timing of input and output signals according to data of the adjustment parameters which are set for the timing adjustment circuit 72a by the program serving as a parameter setting section. The timing adjustment circuit 72a adjusts timing of reference signals for the various drive signals OUT1 with timing corresponding to the set adjustment parameters, outputs the various drive signals OUT1 with the timing corresponding to the set adjustment parameter data, and receives an input signal INP1 with the timing corresponding to the set adjustment parameter data.

The drive circuit 71a and the timing adjustment circuit 72a adjust amplifier gain, an amount of delay of a delay circuit, pulse width, and a duty cycle of pulses according to bit values corresponding to the set adjustment parameter data.

The display controller 65b outputs display data to the LCD 4 via a timing adjustment circuit 72b by driving a drive circuit 71b for the LCD 4. The drive circuit 71b drives the LCD 4 serving as a display section which displays subject's images picked up by the camera 31. The drive circuit 71b outputs the drive signal OUT4 at a voltage corresponding to the set adjustment parameter data. The CPU core 61, the flash memory 63, and the display controller 65b make up a display data output section which outputs display data used to display image data on the LCD 4 via the connector 12.

As with the timing adjustment circuit 71a, the timing adjustment circuit 72b outputs the various drive signals OUT4 with timing corresponding to the set adjustment parameter data and receives the input signal INP4 with the timing corresponding to the set adjustment parameter data.

The graphic processing section 66 includes a character superimposing section 66a.

The cryptographic processing section 67 has a circuit which encrypts and decrypts image data. An encryption processing circuit in the cryptographic processing section 67 performs an encryption process on image data under the control of the CPU core 61 during recording of the image data. A decryption processing circuit in the cryptographic processing section 67 performs a decryption process on image data under the control of the CPU core 61 during reproduction of the image data. Thus, during the reproduction of image data, the display controller 65b of the display data output section outputs the image data decrypted by the cryptographic processing section 67.

The other circuits 68 include a memory card controller 68a, a parallel I/O 68b, a serial I/O 68c, a USB OF 68d, a clock 68e, and a touch panel controller 68f.

The memory card controller 68a is a circuit which controls data input and output to/from the memory card 14.

The parallel I/O (PIO) 68b is an interface circuit used for input of an operation button signal from the operation section 5 as well as for input and output of a parallel signal (not shown). The serial UO (SIO) 68c is an interface circuit used for input and output of a serial signal (not shown). The USB OF 68d is an interface circuit used for input and output of data to/from USB-compatible devices. The clock 68e is a circuit for internal time management.

The touch panel controller 68f outputs the drive signal OUT3 for the touch panel 33 via a drive circuit 71c and timing adjustment circuit 72c for the touch panel 33 and receives the input signal INP3 via the timing adjustment circuit 72c. The drive circuit 71c drives the command input section used to specify the concrete operations of the endoscope apparatus 1 and outputs the drive signal OUT3 at a voltage corresponding to set adjustment parameter data.

As with the timing adjustment circuit 71a, the timing adjustment circuit 72c outputs the various drive signals OUT3 with timing corresponding to the set adjustment parameter data and receives the input signal INP3 with the timing corresponding to the set adjustment parameter data.

Incidentally, the input signals INP sometimes do not need timing adjustment. In such a case, the input signals may be inputted into the video input processor 65 or the other circuits 68 by bypassing the timing adjustment circuit as indicated by two-dot chain lines in FIG. 4.

If data transmission and reception are performed between the camera 31, the LCD 4, or the touch panel 33 and the semiconductor device 22 by LVDS or other serial communications, then LVDS and similar circuits for that are provided between the timing adjustment circuits 72 and the camera 31, the LCD 4, or the touch panel 33.

Furthermore, if the illuminating LED 32 is driven by PWM, an interface for the PWM-driving is included in the other circuits 68 and the semiconductor device 22 drives the LED 32 directly using PWM or drives the LED 32 using a drive circuit provided separately.

Figure 5:
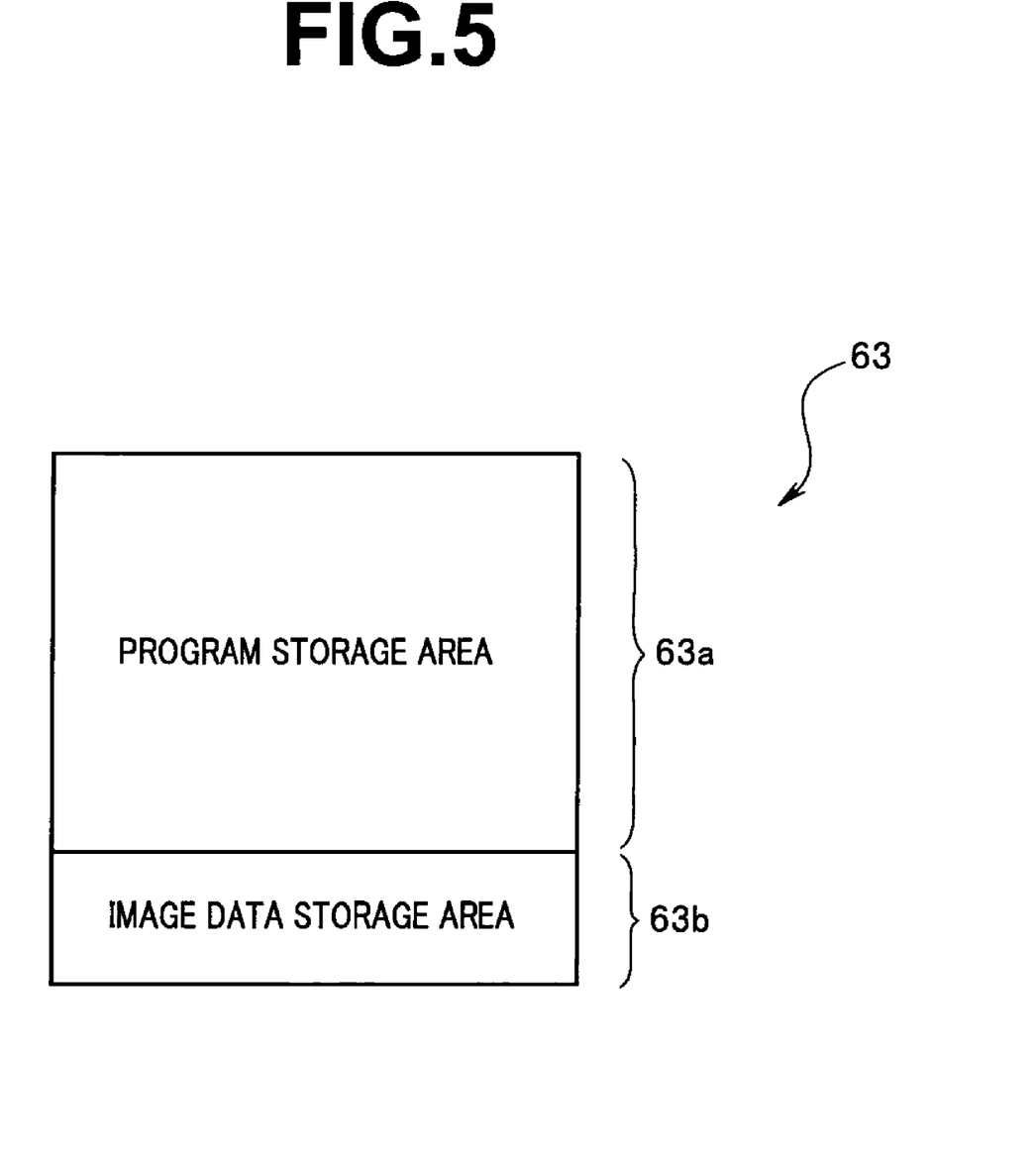
FIG. 5 is a memory map showing a configuration of a storage area in a flash memory 63 according to the embodiment of the present invention.

FIG. 5 is a memory map showing a configuration of a storage area in the flash memory 63. The flash memory 63 includes a program storage area 63a which stores programs and the like for performing the operation of the entire endoscope apparatus 1 and an image data storage area 63b which stores encrypted image data. The programs stored in the program storage area 63a include a program for controlling the operation of the entire endoscope apparatus 1, a program for setting adjustment parameters for the drive circuits and the timing adjustment circuits described above, and a program for recording and reproduction processes of image data described later.

(Operation)

Figure 6:
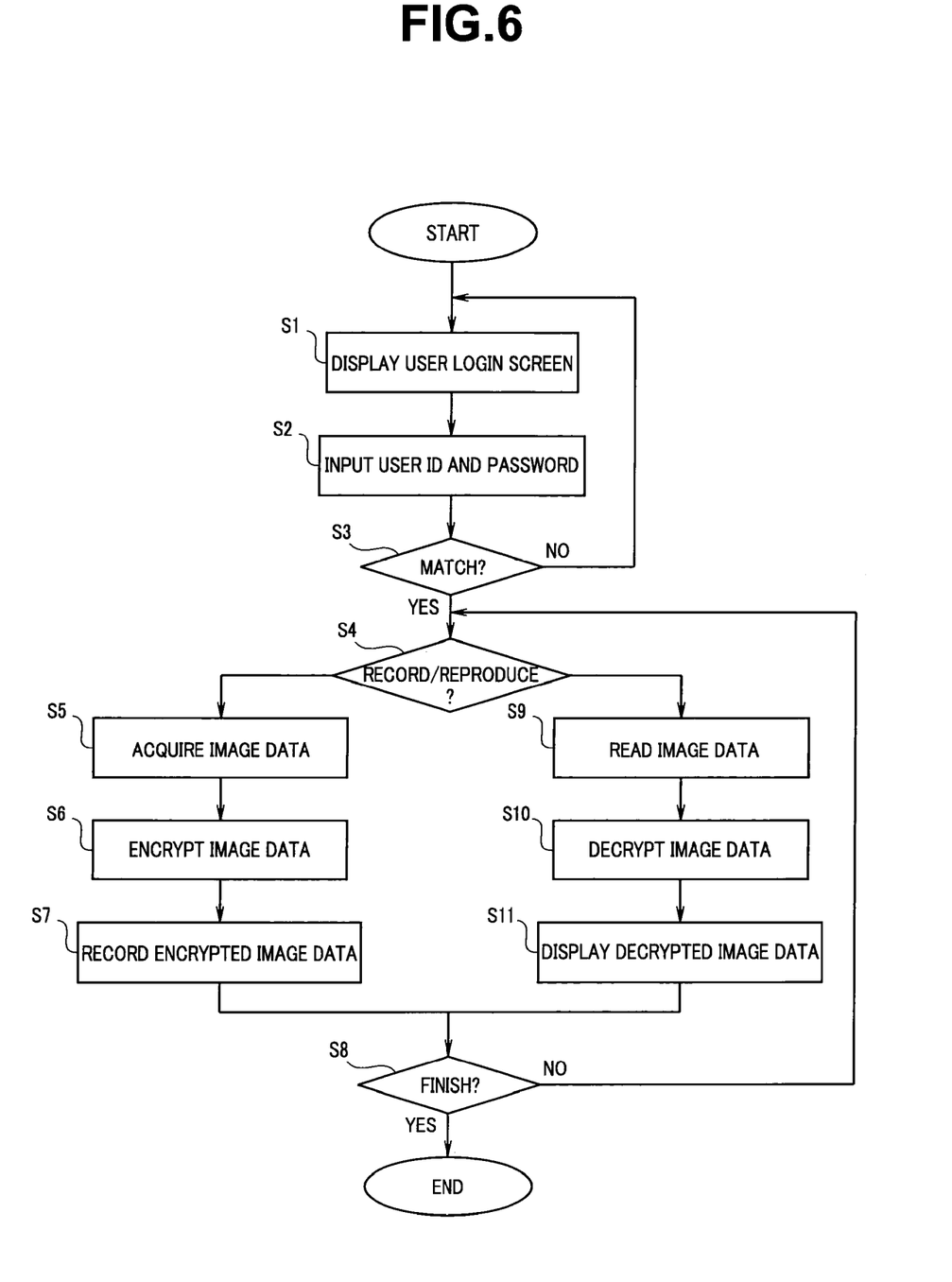
FIG. 6 is a flowchart showing a flow of processes performed by the endoscope apparatus 1 according to the embodiment of the present invention to record and reproduce image data.

Next, the operation of the above-described endoscope apparatus 1 will be described. FIG. 6 is a flowchart showing a flow of processes performed by the endoscope apparatus 1 to record and reproduce image data. The processes in FIG. 6 are performed as the CPU core 61 executes a program by loading the program into the RAM 62 from the program storage area 63a of the flash memory 63 at the direction of the user.

When the user turns on the endoscope apparatus 1, first a user authentication process is performed.

Specifically, as shown in FIG. 6, the CPU core 61 displays a user login screen on the LCD 4 (Step 1; hereinafter "Step" is abbreviated to S). The user login screen (not shown) displays two input fields to input a user ID and a corresponding password, allowing the user to input the user ID and password of the user.

Once the user inputs his/her user ID and password, the CPU core 61 performs input processing on the user ID and the password (S2).

The CPU core 61 performs an authentication process based on the inputted ID and password to determine whether the inputted ID and password match predetermined data (S3).

If there is no match, the authentication fails, and consequently the processing returns to S1. If there are matches, the user is authenticated and allowed to perform inspection using the endoscope apparatus 1. Although the endoscope apparatus 1 has various functions, only an image data recording process and reproduction process will be described here.

The CPU core 61 determines whether the user has issued a command to record or reproduce image data (S4). If the user issues a command to record image data via the touch panel 33 or the operation section 5, the CPU core 61 acquires image data as processed data by processing image pickup data from the camera 31 (S5). As used herein, the term "processed data" can refer to raw image pickup data which has been converted to image data, image data which has been converted to display data, as well as data which has been encoded and/or encrypted. Such is the case when, for example, the user acquires a still image using a freeze button and issues a command to record the still image.

Next, the CPU core 61 encrypts the acquired image data using the cryptographic processing section 67 (S6). The encryption is performed using, for example, a 256-bit AES encryption technology.

The CPU core 61 records the encrypted image data in the flash memory 63 and/or memory card 14 specified by the user (S7). As described above, the endoscope apparatus 1 can record image data in either of the flash memory 63 which is a built-in memory and the memory card 14 which is an external memory.

Then, the CPU core 61 determines whether there is a command to finish processing. If there is no command to finish processing, the CPU core 61 returns to S4 (NO in S8). If processing for finishing is commanded, the CPU core finishes processing (YES in S8).

When the user issues a command to reproduce image data via the touch panel 33 or the operation section 5, the CPU core 61 reads the image data out of the flash memory 63 or the memory card 14 (S9).

Next, the CPU core 61 decrypts the image data read out, using the cryptographic processing section 67 (S10). The decryption is performed using the encryption technology used for the encryption.

The CPU core 61 displays the decrypted image data on the screen of the LCD 4 (S11).

Then, the CPU core 61 determines whether there is a command to finish processing. If there is no command to finish processing, the CPU core 61 returns to S4 (NO in S8). If processing for finishing is commanded, the CPU core finishes processing (YES in S8).

In this way, using the endoscope apparatus 1, the user can record image data by encrypting the image data and display the image on the LCD 4 by decrypting and reproducing the image data.

Thus, although generally image data often contains confidential information, due to each user having a core unit, the endoscope apparatus according to the present embodiment enables to prevent spill of the confidential information.

That is, since the user can lend the endoscope apparatus 1 to another department or an affiliated company by removing a core unit equipped with a built-in memory and an external memory from the body portion, it is possible to prevent spill of confidential information.

Also, endoscope apparatuses, which have been increasingly downsized, might get lost themselves, leading easily to spill of confidential information. However, the endoscope apparatus according to the present embodiment, which allows the core unit equipped with a built-in memory and an external memory to be removed from the body portion, is particularly suitable for highly downsized apparatuses.

The user sometimes asks the manufacturer to inspect or repair the endoscope apparatus 1 if the endoscope apparatus 1 fails or the like. In such a case, the user removes the core unit 11 from the body portion 2 of the endoscope apparatus 1 and hands over the body portion 2 and the scope unit 3 without the core unit 11 to the manufacturer or a manufacturer's inspector.

Figure 7:
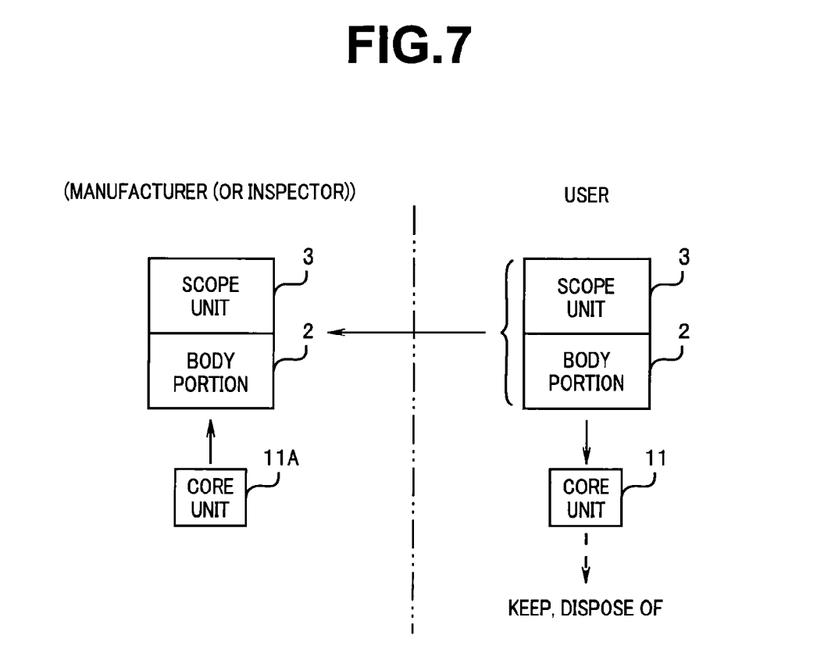
FIG. 7 is a diagram illustrating a flow of a body portion 2, a scope unit 3, and the core unit 11 between a user and a manufacturer in the case of repair or the like, according to the embodiment of the present invention.

FIG. 7 is a diagram for illustrating a flow of the body portion 2, the scope unit 3, and the core unit 11 between a user and a manufacturer in the case of repair or the like. As shown in FIG. 7, the user removes the core unit 11 from the body portion 2 and hands over the body portion 2 and the scope unit 3 to the manufacturer or a manufacturer's inspector. The inspector can conduct inspection and the like using another core unit 11A instead of the user's core unit 11. Generally, the body portion 2 or the scope unit 3 contains a larger number of parts, and thus has a higher probability of failure than the core unit 11.

The inspector attaches the core unit 11A to the body portion 2 and operates the body portion 2 and scope unit 3 of the endoscope apparatus. If there is nothing wrong with the body portion 2 and the scope unit 3, the inspector can determine that there is a possibility of failure in the user's core unit 11. On the other hand, when the body portion 2 and the scope unit 3 are operated using the core unit 11A, if it turns out that something is wrong with the body portion 2 or the scope unit 3, the inspector can repair the body portion 2 or the scope unit 3.

If something is found wrong with the body portion 2 or the scope unit 3 at the manufacturer, when the user receives the repaired body portion 2 or scope unit 3, the user can verify the operation of the endoscope apparatus 1 by attaching the core unit 11 to the body portion 2. When the repaired body portion 2 and scope unit 3 are operated using the user's core unit 11, if the endoscope apparatus 1 does not operate properly, the user or inspector can determine that there is also a possibility of failure in the user's core unit 11.

If the core unit 11 is faulty, the user appropriately disposes of the core unit 11 determined to be faulty, making sure that there will be no leakage of confidential information. The appropriate disposal involves, for example, destroying the core unit 11 under the management of the user so that the image data can no longer be read out. For that, the entire core unit 11 may be broken into fragments or only the part containing the non-volatile memory which stores the image data may be destroyed, using a hammer or the like.

Figure 8:
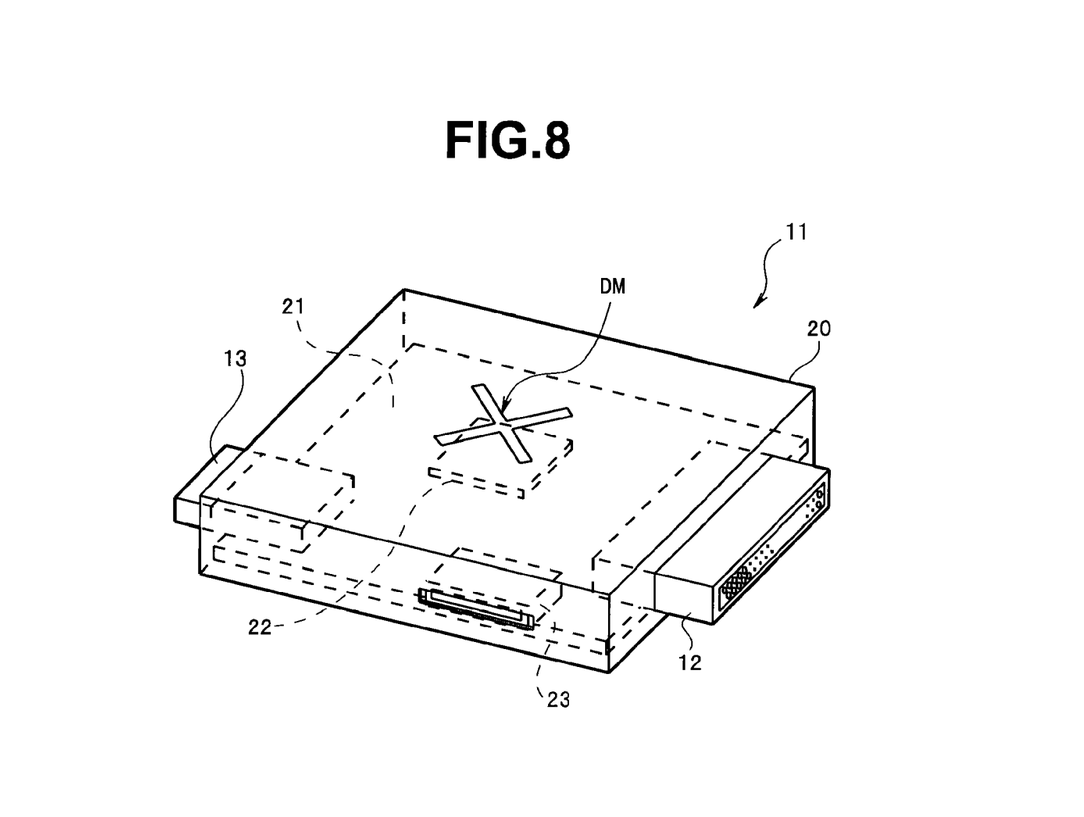
FIG. 8 is an external view of the core unit 11 carrying a mark which indicates a location to be destroyed, according to the embodiment of the present invention.

FIG. 8 is an external view of the core unit 11 carrying a mark which indicates a location to be destroyed. As shown in FIG. 8, a mark DM which indicates a location to be destroyed is printed or engraved, near the flash memory 63 which stores the image data, on a surface of the enclosure 20 of the core unit 11. In FIG. 8, an "X" sign is put on the surface of the enclosure 20, at a location near the semiconductor device 22 incorporating the flash memory 63. If a flash memory 40 is provided on the board 21, a mark DM is provided on the surface of the enclosure 20, not only near the semiconductor device 22, but also near the flash memory 40.

Incidentally, the enclosure 20 may be transparent. A transparent enclosure will allow the user to visually identify the location of a chip to be destroyed from outside the enclosure 20. Furthermore, the enclosure 20 may be a transparent enclosure which carries the mark DM.

The core unit 11, if not faulty, can be connected to a PC to read out image data. As shown in FIG. 2, the core unit 11 can be connected to a PC 41 placed away from the endoscope apparatus, via the USB connector 13.

Figure 9:
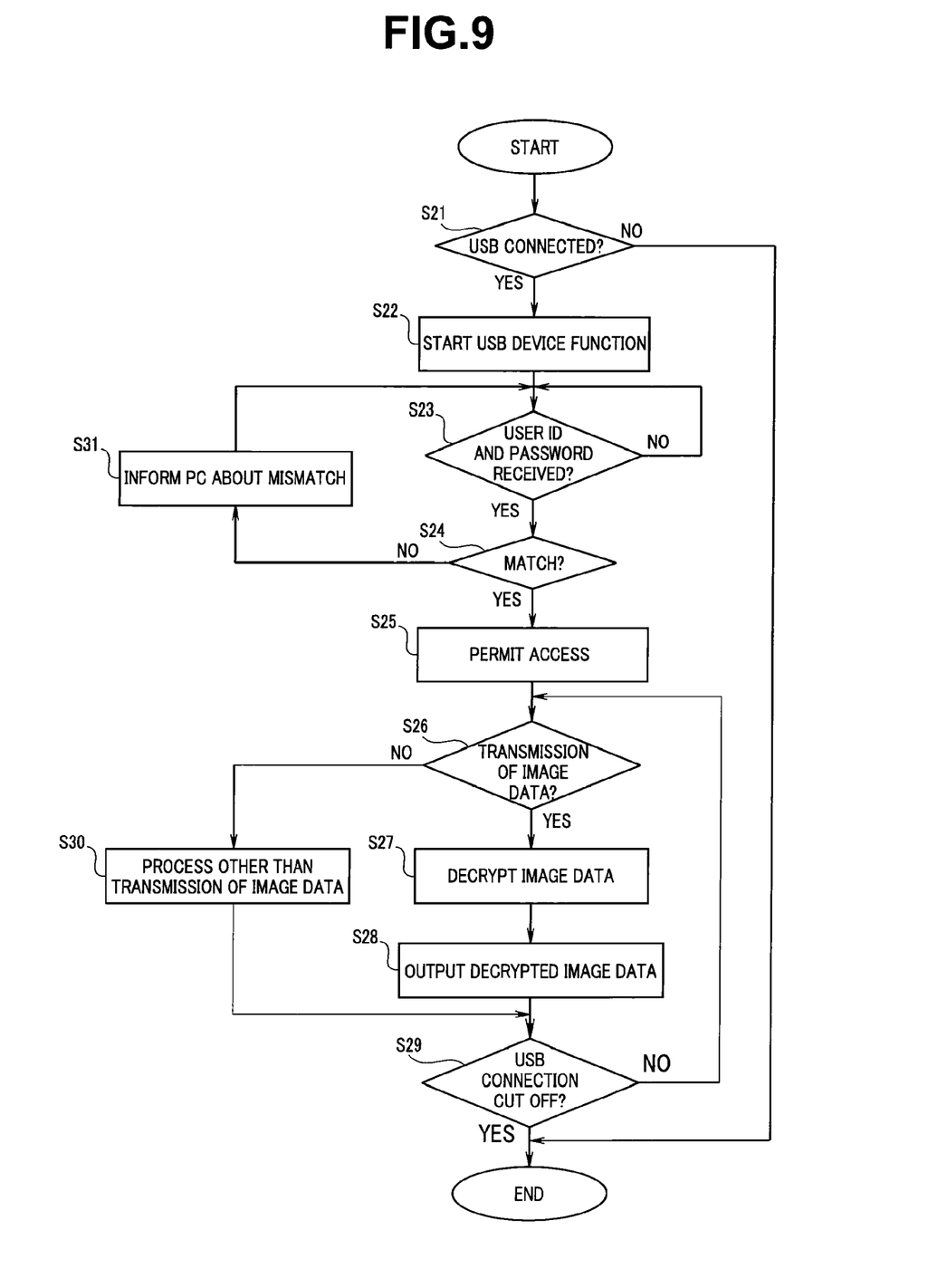
FIG. 9 is a flowchart showing an exemplary flow of processes such as transmission of image data performed by the core unit 11 on instructions from a PC connected to the core unit 11, according to the embodiment of the present invention.

FIG. 9 is a flowchart showing an exemplary flow of processes such as transmission of image data performed by the core unit 11 on instructions from a PC connected to the core unit 11 and serving as a display device.

Once connected to the PC 41, the core unit 11 starts up by being supplied with power from the PC 41. The CPU core 61 can detect that the USB connector 13 has been connected to the PC 41.

The CPU core 61 determines whether or not the USB connector 13 has been connected to a USB connector of the PC 41 (S21). The determination as to the connection of the USB connectors may be made by detecting a state of power supply from the PC 41. If it is determined that the USB connector 13 has been connected to the PC 41, the CPU core 61 starts a USB device function by setting the device function on the USB I/F 68*d* (S22).

If it is not determined that the USB connector 13 has been connected to the PC 41, the CPU core 61 finishes processing as a USB connector connection error without doing anything (NO in S21).

On the PC 41, after the core unit 11 is recognized as a USB device, the user can execute a user login screen generating program of the PC 41 and thereby display a user login screen on a monitor of the PC 41.

If the core unit 11 supports the USB Mass Storage Class, the user login screen generating program may be installed on the core unit 11 and the user may execute the program on the PC 41. The user of the PC 41 can input his/her user ID and password using the user login screen displayed on the monitor.

The CPU core 61 waits for receiving until a user ID and password inputted by the user is received (NO in S23).

If it is determined that a user ID and a password have been received, the CPU core 61 performs an authentication process based on the received user ID and password to determine whether the received user ID and password match predetermined data (S24).

If there is no match, the authentication fails, and consequently the CPU core 61 informs the PC 41 about the authentication failure (S31) and the processing returns to S23. If there are matches, the authentication is successful and the CPU core 61 permits access from the PC 41 (S25).

The CPU core 61 determines whether or not a purpose of the access from the PC 41 is to request transmission of image data (S26). If transmission of image data is requested (YES in S26), the CPU core 61 reads the image data out of the flash memory 63 and decrypts the image data using the cryptographic processing section 67 (S27). The CPU core 61 outputs the decrypted image data via the USB connector 13 (S28). A transfer process of the image data involves, for example, moving or copying the image data to the PC 41.

Then, the CPU core 61 determines whether or not connection between the USB connector 13 and a USB connector of the PC 41 is broken, i.e., whether or not the USB connection is cut off (or whether or not a disconnect request has been received) (S29). If the USB connection is not cut off (NO in S29), the processing returns to S26. If the USB connection is cut off (or a disconnect request has been received), the processing is finished (YES in S29).

If the purpose of the access from the PC 41 is other than to request transmission of image data (NO in S26), the CPU core 61 performs a requested process which is other than transfer (S30). The process other than transfer is, for example, a delete process.

As described above, when used by multiple other departments or an affiliated company, sent for repair, or the like, the endoscope apparatus 1 according to the present embodiment allows the user to remove the core unit 11 incorporating a non-volatile memory which stores image data and hand over only the body portion 2 and the scope unit 3 to the manufacturer. Since the image data is recorded in the flash memory 63 or 40 which is a non-volatile memory in the core unit 11, the image data will not fall into hands of others by mistake. In the case of repair and the like, the manufacturer's inspector can inspect the endoscope apparatus 1 using another core unit instead of the user's core unit.

Also, since the non-volatile memory 63 which stores the image data is incorporated in a single-chip semiconductor device 22, it is extremely difficult to read the image data out of the chip.

Furthermore, since the image data in the non-volatile memory is encrypted, still higher security is available.

Also, if the enclosure 20 carries a mark DM which indicates a location to be destroyed as shown in FIG. 8 or if a transparent enclosure is used allowing a chip location to be identified visually, when disposing of the core unit 11, the user can reliably destroy the non-volatile memory which stores the image data by hitting the location of the enclosure carrying the mark DM with a hammer or the like or hitting the location of the non-volatile memory seen through the transparent enclosure. This provides high security at the time of disposal.

Furthermore, by simply connecting the core unit 11 to a PC via a USB connection, the user can read image data out of the core unit 11.

Figure 10:
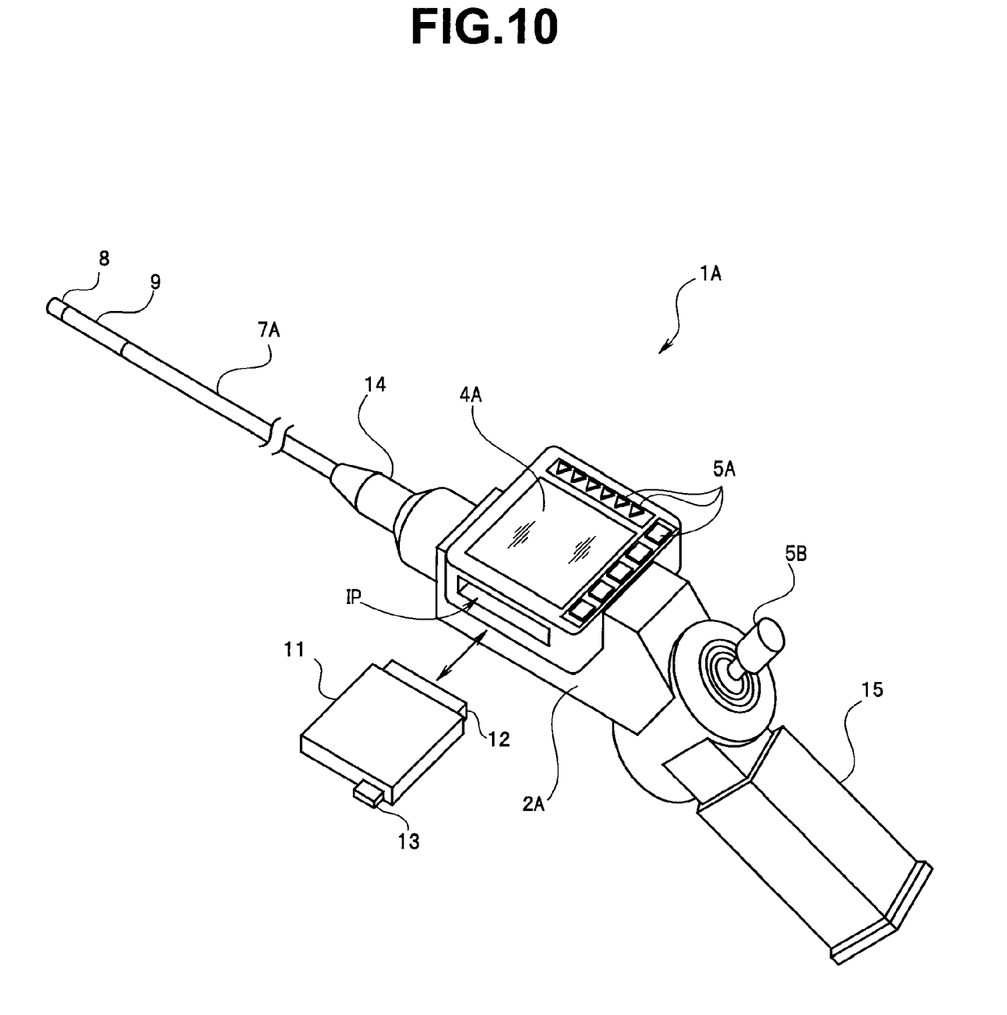
FIG. 10 is an external view of a variation of the endoscope apparatus according to an embodiment of the present invention.

Incidentally, although the endoscope apparatus 1 includes the separate body portion 2 and scope unit 3 with the operation section 5 provided in the scope unit 3, the core unit according to the present embodiment is also applicable to an endoscope apparatus of a configuration such as shown in FIG. 10.

FIG. 10 is an external view of a variation of the endoscope apparatus according to the present embodiment. The endoscope apparatus 1A shown in FIG. 10 includes a flexible or rigid insertion portion 7A and a body portion 2A. A bend preventing portion 14 is provided in a proximal end portion of the insertion portion 7A which is provided by extending from the body portion 2A. In the body portion 2A, an LCD 4A is provided as a monitor while various operation buttons 5A, joystick 5B, and the like are provided as an operation section. Furthermore, the body portion 2A includes a handle 15 as a grasping portion.

The core unit 11 is detachable through an insertion port IP in a lateral portion of the body portion 2A. The core unit 11 has the same configuration as in FIG. 2. Image data picked up by the endoscope apparatus 1A is encrypted and stored in a non-volatile memory in the core unit 11.

When sending the endoscope apparatus 1A for repair or the like, the user can hand over only the body portion 2A together with the insertion portion 7A to the manufacturer by removing the core unit 11.

As described above, the embodiment and variation of the present invention can implement an endoscope apparatus and connection unit therefor which can increase security of the image data in a built-in memory.

The present invention is not limited to the embodiment described above, and various changes and alterations may be made without departing from the scope and spirit of the present invention.

What is claimed is:

1. An endoscope apparatus comprising:
    an endoscope apparatus body portion which includes a first connector, and which is connectable to an insertion portion having an image pickup device disposed at a distal end portion thereof; and
    a connection unit which includes:

a second connector which is removably connectable to the endoscope apparatus body portion by communicating the second connector with the first connector;

a non-volatile memory which stores a program for processing image data inputted from the image pickup device via the second connector;

a CPU which controls the processing of the image data in accordance with the stored program to produce processed data;

a cryptographic processing section which encrypts the image data from the image pickup device and which decrypts the encrypted image data under control of the CPU; and a display data output section configured to output the image data, which is decrypted by the cryptographic processing section, to the endoscope apparatus body portion.

2. The endoscope apparatus according to claim 1, wherein the endoscope apparatus body portion further includes a display device.

3. The endoscope apparatus according to claim 2, wherein the display data output section is configured to output the decrypted image data as display data to the display device via the second connector.

4. The endoscope apparatus according to claim 1, wherein the display data output section is configured to output the decrypted image data via a third connector provided on the connection unit.

5. The endoscope apparatus according to claim 1, wherein the CPU and the non-volatile memory are incorporated in a single-chip semiconductor device.

6. The endoscope apparatus according to claim 1, wherein the non-volatile memory comprises a semiconductor device which is different from a semiconductor device which incorporates the CPU.

7. The endoscope apparatus according to claim 4, wherein the display data output section is configured to transmit the decrypted image data to a personal computer via the third connector.

8. The endoscope apparatus according to claim 1, wherein:
the connection unit comprises a memory connector which is adapted to removably receive an external memory; and
the CPU is configured to record the encrypted image data in the external memory.

9. A connection unit for an endoscope apparatus, the connection unit being removably connectable to an endoscope apparatus body portion of the endoscope apparatus which includes a first connector and which is connectable to an insertion portion having an image pickup device disposed at a distal end portion thereof, the connection unit comprising:
a second connector which is removably connectable to the first connector of the endoscope apparatus body portion;

a non-volatile memory which stores a program for processing image data inputted from the image pickup device via the second connector;

a CPU which controls the processing of the image data in accordance with the stored program;

a cryptographic processing section which encrypts the image data from the image pickup device and which decrypts the encrypted image data under control of the CPU; and a display data output section configured to output the image data, which is decrypted by the cryptographic processing section, to the endoscope apparatus body portion.

10. The connection unit according to claim 9, wherein the display data output section is configured to output the decrypted image data to a display device for display.

11. The connection unit according to claim 10, wherein the display data output section is configured to output the display data to the display device via the second connector.

12. The connection unit according to claim 9, wherein the display data output section is configured to output the decrypted image data via a third connector provided on the connection unit.

13. The connection unit according to claim 9, wherein the CPU and the non-volatile memory are incorporated in a single-chip semiconductor device.

14. The connection unit according to claim 9, wherein the non-volatile memory comprises a semiconductor device which is different from a semiconductor device which incorporates the CPU.

15. The endoscope apparatus according to claim 1, wherein the connection unit further includes a drive circuit which outputs a drive signal to drive the image pickup device via the second connector.

16. The endoscope apparatus according to claim 15, wherein the connection unit inputs the image data from the image pickup device via the second connector.

17. The endoscope apparatus according to claim 16, wherein the connection unit further includes a timing adjustment circuit which adjusts at least one of an output timing of the drive signal to the image pickup device, and an input timing of the image data from the image pickup device.

18. The connection unit according to claim 9, further comprising a drive circuit which outputs a drive signal to drive the image pickup device via the second connector.

19. The connection unit according to claim 18, wherein the connection unit inputs the image data from the image pickup device via the second connector.

20. The connection unit according to claim 19, further comprising a timing adjustment circuit which adjusts at least one of an output timing of the drive signal to the image pickup device, and an input timing of the image data from the image pickup device.

* * * * *